United States Patent
Harper et al.

(10) Patent No.: US 7,891,062 B2
(45) Date of Patent: Feb. 22, 2011

(54) LIP CLOSURE DEVICE FOR USE WITH HUMAN REMAINS AND METHOD OF FORMING SAME

(76) Inventors: Darryl William Harper, 2135 Brook Dr., Kalamazoo, MI (US) 49048; Robert Selvy Harper, Jr., 4189 Durango, Kalamazoo, MI (US) 49048

( * ) Notice: Subject to any disclaimer, the term of this patent is extended or adjusted under 35 U.S.C. 154(b) by 295 days.

(21) Appl. No.: 11/369,387

(22) Filed: Mar. 7, 2006

(65) Prior Publication Data
US 2007/0209171 A1      Sep. 13, 2007

(51) Int. Cl.
*A01N 1/00* (2006.01)
*A61B 17/08* (2006.01)
*A61D 1/00* (2006.01)

(52) U.S. Cl. ............ 27/21.1; 27/22.1; 606/216
(58) Field of Classification Search ............ 27/21.1, 27/22.1; 606/216
See application file for complete search history.

(56) References Cited

U.S. PATENT DOCUMENTS

| | | | | |
|---|---|---|---|---|
| 6,056,778 | A * | 5/2000 | Grafton et al. | 606/77 |
| 6,241,747 | B1 * | 6/2001 | Ruff | 606/216 |
| 6,848,152 | B2 * | 2/2005 | Genova et al. | 29/7.1 |

OTHER PUBLICATIONS

1 Embalming Online Glossary definition of "trocar".*

* cited by examiner

*Primary Examiner*—Melanie J Hand
(74) *Attorney, Agent, or Firm*—Price, Heneveld, Cooper, DeWitt & Litton, LLP

(57) ABSTRACT

A lip closure device (105) for use with human remains includes a shaft (201) having a first end (205) that is substantially pointed and a second end (213) that is substantially blunt. One or more hooking notches (207, 215) are used for engaging with tissue inside the mouth of the human remains in order to maintain the lips into a substantially closed position.

13 Claims, 2 Drawing Sheets

US 7,891,062 B2

LIP CLOSURE DEVICE FOR USE WITH HUMAN REMAINS AND METHOD OF FORMING SAME

FIELD OF THE INVENTION

The present invention relates to the field of embalming instrumentation and more particularly to an instrument for positioning the lips of the deceased in mortuary or funeral services.

BACKGROUND

It is the responsibility of a mortician offering licensed mortuary services to prepare the body of the deceased in a manner in which the body can be viewed. For presentation during visitation, it is desirable that the body of the deceased be viewed with facial features appearing as natural as possible. In cases where embalming has been performed, the remains typically begin to dehydrate in the region of the mouth. Consequently, the deceased's lips may begin to part, making facial features and appearance look unnatural.

One option for handling dehydration around the mouth is a special embalming solution intended to address this problem. However, the use of these types of products can produce a residue that must then be masked to achieve a "natural" look. Since this masking takes place directly on the lips, it becomes very obvious and easy to see. Therefore, this solution only addresses the problem of the parting lips and not the primary responsibility of the mortician, which is to achieve the "natural" look.

Thus, the needs exists to provide a solution for keeping a deceased's upper and lower lips closed for viewing during funeral services without the use of specialized embalming solutions or masking techniques.

SUMMARY OF THE INVENTION

The invention is a lip closure device that addresses two problems presented when human remains begin to dehydrate around the region of the mouth and lips after embalming has been completed: namely, the parting of the lips, and assuring a "natural" look for viewing of the deceased by family, friends and other loves ones during funeral services. The lip closure device includes two shirt ends where one side utilizes a speared edge while the opposite side utilizes a flat edge. The invention also can be used as an aid during the facial feature setting process of embalming. Whether in partnership with internal mouth setting products or not, the invention can be used as a reusable tool for holding facial features in place during the administration of embalming fluid. This assures that the positioning stays consistent with that needed by the mortician.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
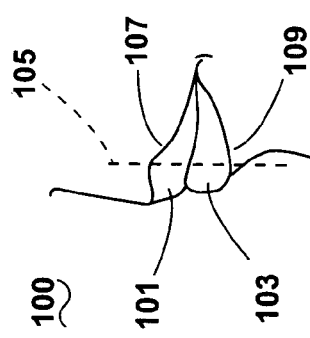
FIG. 1 illustrates a side perspective view of human lips where the invention is inserted substantially vertically to secure the upper and lower lips into a fixed position.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a lip closure device for use with human remains. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element. It is expected that one of ordinary skill, notwithstanding possibly significant effort and many design choices motivated by, for example, available time, current technology, and economic considerations, when guided by the concepts and principles disclosed herein will be readily capable of generating such alternative embodiments with minimal experimentation.

As noted herein, previous techniques and products have fallen short of providing both the proper positioning of the lips as well as a "natural" appearance of the face. Therefore, the present invention has been developed to address both of these concerns. FIG. 1 illustrates a side view of the lips where the invention is used in connection with human remains. Specifically, the facial view 100 includes an upper lip 101 and lower lip 103. The lip closure device 105 as described herein is used to maintain the lips in a closed position by piercing the orbicularis oris 107 above and behind the upper lip 101 as well as piercing the orbicularis oris 109 below and behind the lower lip 103. Those skilled in the art will recognize that the orbicularis oris 107, 109 is located near the midline on the anterior surface of the maxilla and mandible and modiolus at the angle of the mouth. The orbicularis oris 107, 109 encompasses a mucous membrane near the margin of the lips and raphe with buccinator muscle at the modiolus. The obicularis oris 107, 109 operates to narrow the orifice of the mouth, purse the lips and also pucker the lip edges by flexing the incisivus labvi superioris and inferioris nerves.

Figure 2A:
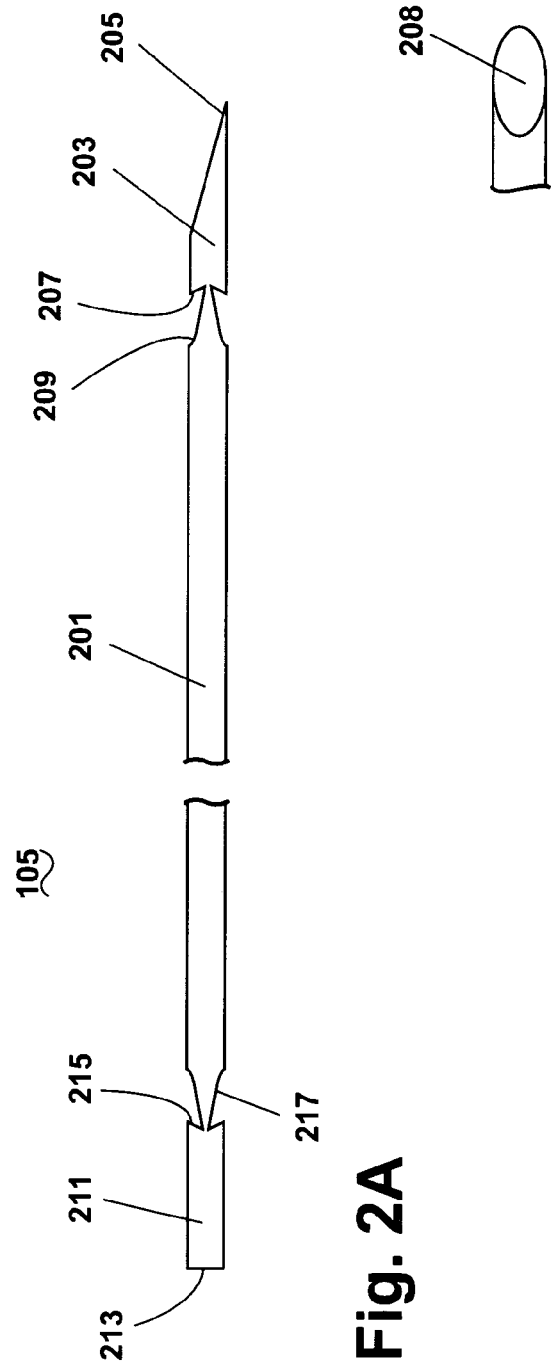
FIG. 2A illustrates a side perspective view of the lip closure device in accordance with an embodiment of the invention.

FIG. 2A illustrates a side view of the lip closure device 105 according to the invention. The closing device utilizes a pin or shaft that is approximately 19 gauge in diameter and approximately three inches in length. Those skilled in the art will recognize that although a three-inch embodiment is shown in FIG. 2A, alternate versions of the invention are also possible where the shaft may be shorter or longer in size.

Figure 2B:
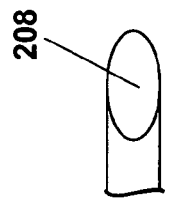
FIG. 2B illustrates a side view of the hypodermic tip as shown in FIG. 2A.

The closure device 105 consists of a shaft 201 having a hypodermic cutting end 203. As best seen in FIG. 2B, the hypodermic cutting end 203 utilizes a cutting edge 205 that has a substantially oval-shaped surface 208. Positioned on the shaft 201 behind the hypodermic cutting end 203, a first hooking notch 207 is cut in a section of the shaft 201 by reducing shaft diameter. The first hooking notch 207 is positioned such that it faces in a direction away from the cutting edge 205. The first hooking notch 207 includes first shaft edges 209 located where the diameter of the shaft 201 is reduced before connecting into the rear of the hypodermic cutting tip 203. The reduction in shaft diameter is accomplished by cutting a wedge from the shaft 20 such that the shaft edges 209 are formed. The first shaft edges 209 allow the hooking notch 207 to be positioned in a space or gap created where the shaft 201 and hypodermic cutting tip 203 are joined.

Figure 3:
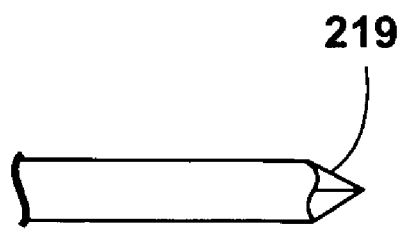
FIG. 3 illustrates a side view of an alternative embodiment of the invention utilizing a tri-facet trocar-style tip.

On the opposite end of the hypodermic cutting end 203 is a blunt cutting end 211 having a blunt edge 213. Similar to the hypodermic cutting end 203, a second hooking notch 215 is positioned behind the blunt cutting end 211. The second hooking notch 215 is formed by using second shaft edges 217 where the diameter of the shaft 201 is reduced at the point it connects to the rear of the blunt cutting end 211. The second shaft edges 217 are cut around circumference of the shaft 201, facing away from the blunt cutting end 211. The second shaft edges 217 are then positioned in the gap or notch created where the shaft diameter is reduced. As seen in FIG. 2A, both of the hooking notches 207, 215 are substantially V-shaped hooks whose ends point in a direction opposite to ends of the closure device 105 in which they are positioned As best seen in FIG. 3, the hypodermic cutting end 203 can be replaced with a tri-facet trocar-style tip 219. The trifacet trocar-style tip 219 offers an advantage in that less force is required to puncture the tissue above or below the lip when positioning the lip closing device 105. Although, the oval tip described in FIG. 2A and the tri-facet trocar-style tip shown in FIG. 3 have been described herein, skilled artisans will recognize that other tip sizes and shapes are possible and within the scope of the invention.

In practice, FIG. 1 illustrates the use of a longer three-inch closing device 105 where the device is initially positioned to force the hypodermic cutting end 203 into the orbicularis oris, which is the tissue immediately above where the lower lip joins with the upper chin. In this example, the closing device punctures the tissue with force applied in an upper direction toward the lip below the nose (not shown). The closing device is positioned so that the first hooking notch 207 is directed between the lips and the teeth (not shown). The tissue inside the lip is then fastened to the first hooking notch 207. The blunt edge 213 is then positioned between the teeth and lower lip holding the mouth and lips in a substantially closed position. The second hooking notch can be fastened to the tissue inside the mouth adjacent to the lower lip. Those skilled in the art will recognize that this procedure can also be performed in the reverse direction with the hypodermic cutting end 103 positioned downward in the tissue between the teeth and lower lip.

Figure 4:
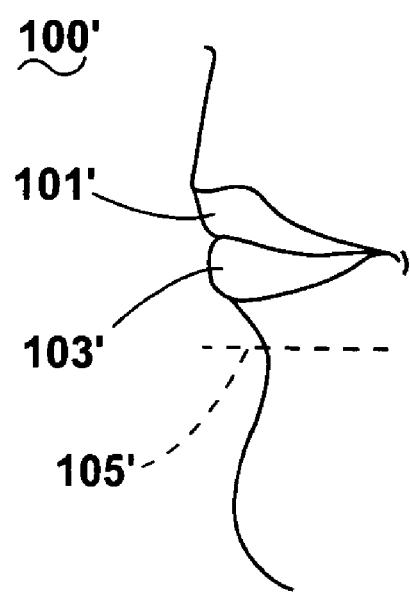
FIG. 4 illustrates a side perspective view of human lips where the invention is depicted in a shorter embodiment of that shown in FIG. 2A and is inserted in a substantially horizontal position in order to secure the lower lip into a fixed position.

As shown in FIG. 4, another embodiment of the invention uses a shorter closing device 105' that is approximately one inch in length. In this example, a hypodermic cutting end will be forced straight back laterally to a point just below the lower lip 103', between the teeth (not shown) and the lower gum line (not shown). This alternative procedure allows the lower lip 103' to be held into a fixed position in relation to the upper lip 101'. Those skilled in the art will further recognize that either of these procedures will secure the lips in the mortician's desired position thereby solving any issue with lip separation during embalming or visitation.

In that the invention is 19-gauge metal stock material that is only a fraction of an inch in diameter, the puncture hole created in the upper or lower lip is extremely small and very simple to conceal. This process uses only a very minute amount of facial masking material in and around the puncture hole. Thus, due to its diminutive size, concealment of the insertion hole can be easily achieved using wax and/or cosmetic masking makeup. Since the hole is not directly on the lips, this masking technique is discreetly concealed. This assures a more "natural" look of the face. Additionally, upon completion of the embalming process, the mortician can remove the closure device whereupon it can be cleansed and stored for future use.

Thus, the present invention describes an instrument to be used in positioning the lips of human remains after embalming is completed in order to maintain the lips of remains in a substantially closed position. The invention permits the facial features to maintain their natural appearance during funeral services and the like.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A lip closure device for use with human remains comprising: a shaft having a first end that is a substantially pointed blade comprised of a first side edge that is aligned with a side of the shaft and second side edge forming a taper with the first side edge and a second end that includes a substantially blunt blade formed at the outer edge of the second end; a first plurality of hooking notches positioned behind the first end and a second plurality of hooking notches positioned behind the second end for engaging with tissue in the human remains to maintain the lips of the human remains into a substantially fixed position; and wherein the first plurality of hooking notches and the second plurality of hooking notches include a notched section having a substantially wide end and a substantially narrow end forming a taper in the shaft with sides that are equidistant from a center point of the shaft such that the first plurality of hooking notches and the second plurality of hooking notches are formed at the substantially narrow end of the notched section.

2. A lip closure device as in claim 1, wherein the first end utilizes a tip having a hypodermic shape that is substantially oval in cross-section.

3. A lip closure device as in claim 1, wherein the first end utilizes a trocar tip.

4. A lip closure device for maintaining the lips of human remains in a closed position comprising: an elongated shaft; a first blade comprised of a straight side edge that is aligned with a side of the elongated shaft and a tapered side edge that forms a taper with the straight side edge and attached to one end of the shaft; a second blade having a blunt end attached to an outer edge at the opposite end of the shaft; and a first plurality of hooking notches and second plurality of hooking notches that each include a notched section having a substantially wide end and a substantially narrow end forming a taper in the elongated shaft with sides that are equidistant from a center point of the shaft such that the first plurality of hooking notches and the second plurality of hooking notches are formed in the narrow end of the notched section where the first plurality of hooking notches and the second plurality of hooking notches are positioned substantially behind the first blade and second blade respectively.

5. A lip closure device as in claim 4, wherein the first blade includes a substantially pointed tip.

6. A lip closure device as in claim 5, wherein the substantially pointed tip is a hypodermic tip.

7. A lip closure device as in claim 5, wherein the substantially pointed tip is a trocar tip.

8. A lip closure device as in claim 4, wherein the second blade includes a substantially blunt tip.

9. A lip closure device as in claim 8, wherein the substantially blunt tip is square.

10. A lip closure device for use with human remains comprising: a shaft having a first end~with a substantially pointed blade comprised of a straight side edge that is aligned with a side of the shaft and a tapered side edge that forms a taper with the first side edge and a second end that is a substantially straight blade having a flat edge formed at the outer edge of the second end; a first plurality of hooking notches positioned behind the first end and a second plurality of hooking notches positioned behind the second end for engaging with tissue within the mouth of the human remains for maintaining the lips of the human remains into a substantially fixed position; and wherein the first plurality of hooking notches and the second plurality of hooking notches include both a notched section having a substantially wide end and a substantially narrow end forming a taper in the shaft with sides that are equidistant from a center point of the shaft such that the first plurality of hooking notches and the second plurality of hooking notches are positioned substantially behind the pointed blade and straight blade respectively and their respective notched section points away from the respective first end and second end of the shaft.

11. A lip closure device as in claim 10, wherein the pointed blade has a hypodermic tip.

12. A lip closure device as in claim 10, wherein the pointed blade has a trocar tip.

13. A lip closure device as in claim 10, wherein the straight blade has a square tip.

* * * * *